US00PP08603P

United States Patent [19]

Benardella

[11] Patent Number: Plant 8,603

[45] Date of Patent: Feb. 22, 1994

[54] MINIATURE ROSE PLANT NAMED BENMAGIC

[75] Inventor: Frank Benardella, Old Tappan, N.J.

[73] Assignee: Nor'East Miniature Roses, Inc., Rowley, Mass.

[21] Appl. No.: 986,242

[22] Filed: Dec. 7, 1992

[51] Int. Cl.[5] ..... A01H 5/00

[52] U.S. Cl. ..... Plt./7.1

[58] Field of Search ..... Plt. 7.1

*Primary Examiner*—Howard J. Locker

*Attorney, Agent, or Firm*—Christie, Parker & Hale

[57] ABSTRACT

A new miniature rose with red and white bicolor flowers of good form.

1 Drawing Sheet

SUMMARY OF THE INVENTION

The present invention relates to a new and distinct variety of rose plant of the miniature rose class, which was created by me by crossing as seed parent the variety known as 'Dickmickey' and as pollen parent the variety known as 'Tinseltown'. The varietal denomination of this new rose is 'Benmagic'.

'Tinseltown' is a red and white striped hybrid tea whose parents are the varieties known as 'Imbroglio' and 'Laguna'. 'Dickmickey' is an orange red patio type rose with slight fragrance, small medium green glossy foliage and bushy growth.

Among the novel characteristics possessed by this new variety which distinguishes it from its parents and all other varieties of which I am aware is its unusual red and white bicolor flowers of good form. 'Benmagic' has very firm substance and usually remains at about the half open stage until it loses substance.

Asexual reproduction by propagation of cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character. Phenotypic expression may vary with light availability and cultural conditions.

DETAILED DESCRIPTION OF THE NEW VARIETY

The foregoing is a detailed description of my new variety, with color terminology in accordance with The Royal Horticultural Society Colour Chart (R.H.S.C.C.). The terminology used in color description herein refers to plate numbers in the aforementioned color chart.

Parentage:

*Seed parent.*—'Dickmickey'.

*Pollen parent.*—'Tinseltown'.

Class: Miniature.

The following observations are made of specimens grown outdoor in Essex County, Mass., during the month of August.

Flower

Blooming Habit: Continuous.

A. Bud:
- (1) *Size.*—Medium.
- (2) *Form.*—Ovoid, pointed.
- (3) *Color.*—As sepals divide, bud color is near 56C edged with near 54A.
- (4) *Sepals.*—Smooth, slightly longer than bud.
- (5) *Peduncle.*—Length— about 1½ inches. Aspect— straight. Strength— erect. Color— near 144A.

B. Bloom:
- (1) *Size.*—Average size when fully expanded— about 1¼ inches.
- (2) *Borne.*—Singly and several together in sprays of three to five blooms.
- (3) *Form.*—High-centered at first, outer petals initially loosely roll under, does not usually open beyond half-open stage.
- (4) *Petalage.*—Number of petals under normal conditions— about 27 to 30.
- (5) *Color.*—After sepals divide and petals open, inner petals at center of flower and outer petals appear as near white edged with near 45A. Reverse of petals appears as near white edged with near 45C. Color at base of petals toward point of petal attachment is near 1B. General tonality from a distance is a red-and-white bicolor. As flowers age, there is substantially no color change after three or more days.

C. Petals:
- (1) *Texture.*—Thick.
- (2) *Appearance.*—Inside velvety and outside satiny.
- (3) *Form.*—Wide fan-shaped, without point at apex.
- (4) *Arrangement.*—Imbricated-regularly arranged, shingle-like.
- (5) *Petaloids in center.*—Few.
- (6) *Persistence.*—Drop off cleanly.
- (7) *Fragrance.*—None.
- (8) *Lasting quality.*—Long as a cut flower and very long lasting on plant.

Reproductive Organs

A. Stamens, filaments and anthers:
- *Arrangement and color.*—Regularly arranged around styles. Color.— near 163C.

B. Pollen:
- *Color.*—Near 163B.

C. Styles: Medium length, even length.

D. Stigmas:

*Color.*—Near 195D.

E. Hips:

*Shape.*—Globular.

*Size.*—Ordinary.

*Color.*—Near 28B to near 28C. *Seed.*—no.

Plant

A. Form: Upright, compact.

B. Growth: Very vigorous.

*Height attained.*—About 18–22 inches.

C. Foliage: Compound 5 to 7 leaflets.

(1) *Size.*—Large.

(2) *Quantity.*—Abundant.

(3) *Color.*—New foliage: Upper side— near 146A. Underside— near 147C. Old foliage: Upper side— near 137A to 136A. Underside— near 147B.

(4) *Shape.*—Oval, pointed.

(5) *Texture.*—Upper side is glossy; underside is matte.

(6) *Edge.*—Serrated.

(7) *Serration.*—Fine and regular.

(8) *Leaf stem.*—Color— near 137C. Underside— 144A.

(9) *Stipules.*—Medium length, not bearded.

(10) *Resistance to disease.*—Blackspot— Average. Mildew— Average. Rust— Average.

D. Wood:

(1) *New wood.*—Color— Near 146B. Bark— Smooth.

(2) *Old wood.*—Color— Near 147B. Bark— Smooth.

E. Thorns:

(1) *Thorns.*—Quantity (main stalk)— ordinary. On laterals from stalk— few. Form— short, downward curve. Length— medium. Color— near 177D. Position— irregular.

(2) *Prickles.*—None.

F. Winter hardiness: Needs protection in severe climates.

I claim:

1. A new and distinct variety of rose plant of the miniature rose class, substantially as shown and described.

* * * * *

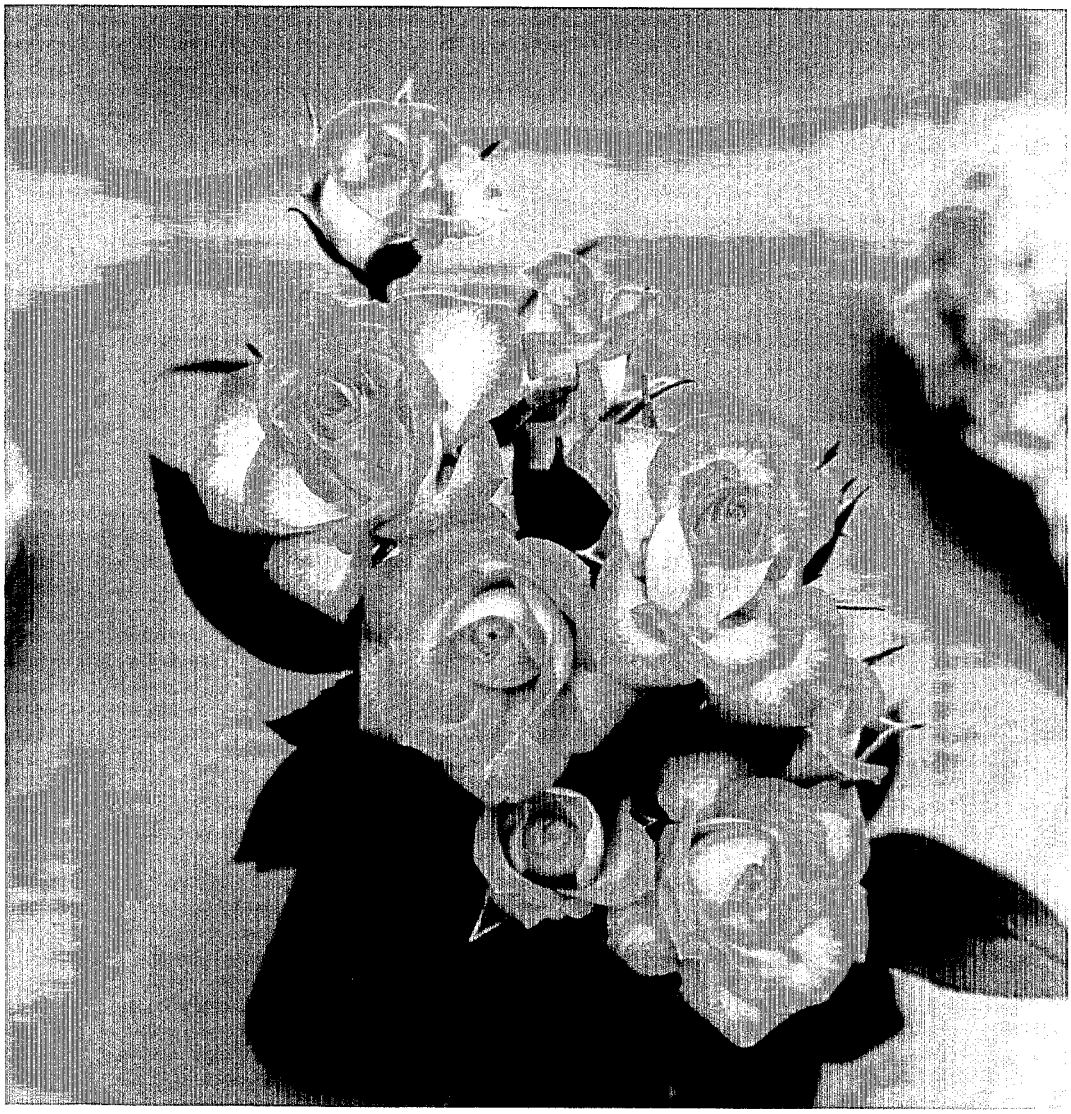

UNITED STATES PATENT AND TRADEMARK OFFICE

CERTIFICATE OF CORRECTION

PATENT NO. : Plant 8,603

DATED : February 22, 1994

INVENTOR(S) : Frank Benardella

It is certified that error appears in the above-indentified patent and that said Letters Patent is hereby corrected as shown below:

Column 1, line 36, change "foregoing" to -- following --.

Signed and Sealed this

Eighteenth Day of October, 1994

Bruce Lehman

*Attest:*

BRUCE LEHMAN

*Attesting Officer*

*Commissioner of Patents and Trademarks*